US005505717A

United States Patent [19]
Moore

[11] Patent Number: 5,505,717
[45] Date of Patent: Apr. 9, 1996

[54] URINARY DRAINAGE DEVICE

[76] Inventor: Patrick S. Moore, 90 Morning Side Dr., Apt. 3-J, New York, N.Y. 10027

[21] Appl. No.: 122,714

[22] Filed: Sep. 15, 1993

[51] Int. Cl.⁶ ............................................. A61F 5/44
[52] U.S. Cl. ........................ 604/349; 128/760; 604/329
[58] Field of Search ............................. 604/329–331, 604/349–353, 276, 320, 321; 128/760, 761, 766–768, DIG. 6

[56] References Cited

U.S. PATENT DOCUMENTS

| | | | |
|---|---|---|---|
| 2,397,257 | 3/1946 | Goland et al. | 128/276 |
| 3,319,684 | 5/1967 | Calhoun | 150/8 |
| 3,774,611 | 11/1973 | Tussey et al. | 128/278 |
| 3,800,795 | 4/1974 | Walker | 128/275 |
| 3,875,941 | 4/1975 | Adair | 128/278 |
| 4,141,361 | 2/1979 | Snyder | 128/278 |
| 4,227,533 | 10/1980 | Godfrey | 604/247 |
| 4,438,763 | 3/1984 | Zablen | 128/DIG. 6 |
| 4,710,169 | 12/1987 | Christopher | 604/349 |
| 4,981,474 | 1/1991 | Bopp et al. | 604/133 |
| 5,019,059 | 5/1991 | Goldberg et al. | 604/317 |
| 5,318,550 | 6/1994 | Cermak et al. | 604/349 |

FOREIGN PATENT DOCUMENTS

| | | | |
|---|---|---|---|
| 0990166 | 6/1976 | Canada | 604/350 |
| 2048680 | 12/1980 | United Kingdom | 604/350 |

Primary Examiner—Randall L. Green
Assistant Examiner—Rob Clarke
Attorney, Agent, or Firm—Greenlee and Winner

[57] ABSTRACT

The invention relates to an improved urinary drainage device which simulates the normal, non-catheterized urethra. This novel design significantly reduces the risk of urinary tract infection typically associated with internal catheters by providing a double-lumen drainage duct with a collapsible inner tube and an evacuator-type collection receptacle. Like the non-catheterized urethra, the inner tube collapses after urination to expel residual urine.

15 Claims, 4 Drawing Sheets

URINARY DRAINAGE DEVICE

FIELD OF THE INVENTION

The present invention relates generally to urinary drainage devices. More particularly, this invention relates to an apparatus for reducing the likelihood of urinary tract infection during continuous urine collection using a collapsible catheter duct.

BACKGROUND OF THE INVENTION

Various devices are known in the art for draining and collecting fluids from body cavities, including collection systems specifically designed for urinary bladder drainage. Most such urine collection devices are simple in design, consisting of a flexible catheter duct connected to a urine receptacle. The catheter duct is inserted through the urethra into the urinary bladder, and urine flows in small quantities as it is produced through the catheter into the receptacle. Unfortunately, these conventional drainage devices often become contaminated during use and infection then ascends in a retrograde manner from the collection receptacle to the patient via the catheter duct. Conventional catheter designs also permit back flow of urine from the receptacle into the bladder, particularly when the catheter duct is elevated above the bladder. Moreover, the urine can remain stagnant in the indwelling catheter of existing devices for extended periods, where microorganisms quickly proliferate at body temperatures. Because the urethra cannot close with existing catheters, catheterized patients experience notoriously high rates of urinary tract infections. None of the current catheter designs simulate the normal urethra, which collapses after urination to expel residual urine, nor do they provide a means for preventing bacterial ingress from the catheter into the urinary bladder.

Evacuator-type drainage devices have been designed to minimize the back flow of fluid from the receptacle. Examples include U.S. Pat. Nos. 2,397,257 (Goland et al.), 3,774,611 (Tussey et al.), 3,875,941 (Adair), 4,141,361 (Snyder), 4,981,474 (Bopp et al.), and 5,019,059 (Goldberg et al.), disclosing bellows-type collection receptacles which act as reservoirs for receiving and collecting the body fluids. These collapsible bellows-type receptacles collect fluid as they return to their original shape. As additional fluid is collected, the weight of the fluid expands the bellows container thereby creating additional partial vacuum to draw additional fluid into the receptacle. None of these devices, however, prevent microbial ingress from this stale fluid into the body cavity. Assuming the negative pressure is generally sufficient to withdraw fluid from the indwelling duct, the suction mechanism can fail during operation (e.g., during handling or emptying of the receptacle) causing retrograde leakage of contaminated fluid into the catheter duct. The potential for infection is further increased with evacuator-type drainage devices since these devices typically require periodic opening to purge fluid and resume the suction, thereby exposing the closed drainage system to the surrounding atmosphere. Finally, the catheter duct in these devices can crimp adjacent to the receptacle in such a way that flow into the receptacle is inhibited, subsequently increasing the risk of back flow and infection.

Other "improved" drainage devices employ check valves which are positioned between the catheter duct and fluid receptacle and are designed to minimize back flow of fluid from the receptacle. Most existing check valves consist of a rubber tube sealed in the inlet neck of the receptacle and projecting into the receptacle. The walls of the valves are normally collapsed to prevent reverse flow but open to permit the flow of fluid into the receptacle under pressure. Examples include U.S. Pat. No. 3,298,370 (Beatty) which discloses a shielded check valve to minimize accidental closures, U.S. Pat. No. 3,312,221 (Overment) which discloses an improved "flutter" valve, and U.S. Pat. No. 3,967,645 (Gregory) which discloses a rigid plastic valve having increased sensitivity to back pressure. Although drainage devices having check valves at the receptacle inlet may successfully minimize back flow of receptacle contents into the catheter duct, such devices are deficient in several respects. First, as with other prior art drainage devices, the catheter ducts often become contaminated during use and infection then ascends in a retrograde manner into the urinary bladder. The catheter duct thus provides an open passage for bacterial ingress into the urinary tract. Second, urine can remain stagnant for extended periods in the indwelling duct, where bacteria quickly proliferate at body temperature. While these check valves may reduce back flow from the receptacle, they do not prevent back flow of contaminated urine from the duct into the bladder. Urinary tract infections are therefore common in patients using such drainage devices. Third, because the check valves in these devices are positioned at the distal end of the catheter duct, the valves themselves are susceptible to accidental closure from external pressure. Outside forces, including the patient or his clothing, may bear on the valve in such a way that flow into the receptacle is inhibited and back flow may occur because the valve is effectively held closed.

U.S. Pat. No. 3,800,795 (Walker) discloses another "improved" urinary drainage collecting device, the improvement comprising a leaf-type check valve at the receptacle inlet to prevent back flow and a complex ventilation system designed to minimize urine in the catheter duct. This design, however, suffers from the aforementioned disadvantages, namely those associated with an indwelling, non-collapsible catheter duct and an external check valve at the receptacle inlet.

A need therefore exists for a device for draining urine from incontinent patients which simulates the normal, non-catheterized urethra. Specifically, a need exists for a device which collapses after urination to expel residual urine from the urethral cavity, eliminates urine back flow into the bladder, and minimizes the risk of retrograde infection from the drainage device into the urinary tract.

SUMMARY OF THE INVENTION

Briefly stated, the present invention provides an improved urinary drainage device which simulates the normal, non-catheterized urethra. This novel design significantly reduces the risk of urinary tract infection typically associated with internal catheters by providing a double-lumen drainage duct with a collapsible inner lumen. Like the non-catheterized urethra, the inner lumen collapses after urination to expel residual urine.

Another principal aspect of this invention is to provide an improved urinary drainage device which prevents urine back flow from the drainage duct into the bladder and minimizes the risk of retrograde infection from the duct into the urinary tract. The present invention provides a simple, double-lumen catheter comprising an inner lumen which collapses after urination to prevent fluid entry and bacterial ingress into the bladder.

Still another principal aspect of this invention is to provide an improved urinary drainage device which closes at the proximal or inlet end of the drainage duct to prevent urine back flow and bacterial ingress into the bladder. In a preferred embodiment, the drainage device comprises at least one unidirectional valve means positioned at or near the proximal or inlet end of the drainage duct. The valve means consists of multiple flexible flaps attached to the inner lumen of the drainage duct near the inlet, projecting towards the distal or receptacle end of the duct. The valve means preferably comprises a pair of overlapping flaps. The flaps are normally closed to prevent reverse flow into the bladder, but open to permit the flow of urine into the duct under very slight pressure. In another preferred embodiment, the proximal or inlet end of the drainage device comprises an elastic, collapsible "O ring"-type portal, such as that in the neck of a rubber balloon. This elastic portal normally contracts to prevent fluid back flow, but it expands and opens under pressure to permit the flow of urine into the duct.

Yet another aspect of the invention is to minimize retrograde infection and back flow of urine using a suctioning means. The suctioning means as used herein comprises an evacuator-type collection receptacle, said collection receptacle comprising a resilient bellows container for receiving and collecting the urine. The bellows container is attached at the top to a rigid support frame, and connected at its base to the frame by slidable rings. As the container collects urine, the weight of the additional urine extends the bellows container, thereby creating additional partial vacuum to draw additional fluid into the receptacle. When used in combination with the collapsible catheter of the present invention, the partial vacuum created during collection facilitates the evacuation and collapse of the catheter.

Another aspect of the invention is to minimize discomfort for the catheterized patient by providing a removable outer catheter shell. In accordance with this aspect of the invention, the double-lumen drainage duct further comprises a removable outer tube or stent. Like existing catheter devices, the outer tube is flexible but firm, permitting insertion into the urethra. Unlike existing devices, however, the outer catheter tube can be removed after insertion leaving only the collapsible inner lumen, which comfortably conforms to the size and shape of the patient's urethra.

The exact nature of this invention as well as other features and advantages thereof will be readily apparent from consideration of the specification, including the drawings. Those of skill in the art will appreciate that the invention described herein is susceptible to many modifications and variations without departing from its scope as defined by the appended claims.

BRIEF DESCRIPTION OF THE DRAWINGS

The accompanying drawings illustrate preferred embodiments of the invention, wherein.

DESCRIPTION OF THE PREFERRED EMBODIMENTS

Figure 1:
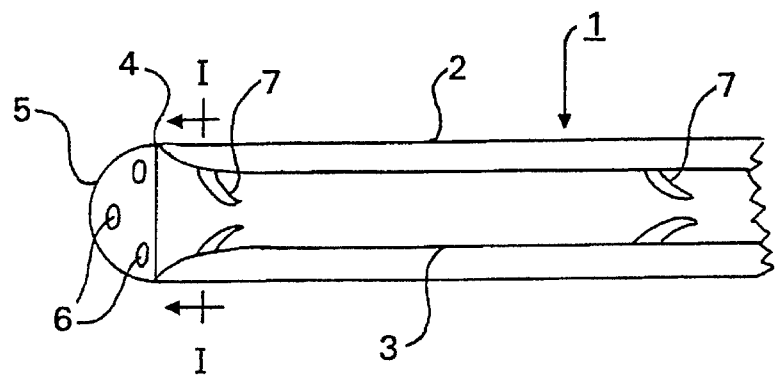
FIG. 1 is a sectional view of the urinary drainage device in an embodiment of the present invention.

Referring now to the drawings, like numbers indicate like features and the same number appearing in more than one figure refers to the same element.

Figure 2:
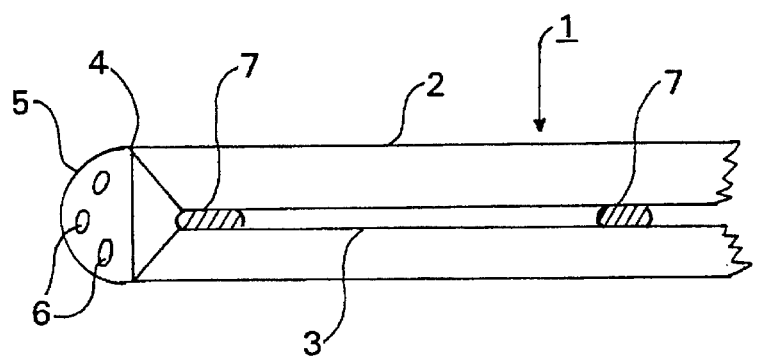
FIG. 2 is a view similar to FIG. 1, but illustrating the inner lumen in collapsed position.

FIGS. 1 and 2 illustrate a drainage duct 1 comprising a flexible outer tube 2 and a collapsible inner tube 3 in the urinary drainage device of the present invention. The inner tube 3 opens during bladder contractions to facilitate urine flow, as shown in FIG. 1, then collapses after urination to expel residual urine and prevent back flow, as shown in FIG. 2. The collapsible inner tube 3 thus simulates the natural urethra, eliminating the risk of retrograde infection commonly associated with urinary drainage devices.

The drainage duct 1 is a cylindrical tube having an inlet or proximal end 4 and a receptacle or distal end (not shown) removably connected to a fluid collection receptacle (not shown). The proximal end 4 terminates in a rounded head 5, said head preferably comprising multiple apertures 6 to reduce the risk of injury to the urinary bladder epithelium due to localized suction. The proximal end 4 of the drainage duct 1 further comprises an anchoring means (not shown), such as an expandable elastic collar, for anchoring the drainage device within the bladder. The anchoring means communicates with an inlet port (not shown) via an internal lumen (not shown) formed within the outer tube 2. The inlet port is removably connected to an inflating means (not shown) for inflating said elastic collar and anchoring said drainage duct 1 after insertion. The elastic collar is deflated prior to withdrawing the drainage device by attaching a suctioning means to the inlet port and creating a vacuum therein. The use of an expandable anchoring means is customary in the art, the construction and use of which is a matter of ordinary skill.

The outer tube 2 is formed of a flexible rubber latex or plastic biocompatible material, as is known in the art. The inner tube 3 may be formed of any flexible polymeric non-toxic material. Preferably, the inner tube 3 is made of a hydrophobic material or has an interior surface coating of a hydrophobic substance such as a silicone. The hydrophobic material or inner coating minimizes residual urine retention which might otherwise occur as a thin film between the collapsed walls of inner tube 3. Some degree of self-adherence of the inner surface of inner tube 3 is desirable to maintain a collapsed state in the absence of urine flow and to prevent retention of a film of urine between the collapsed inner walls. However, the self-adherence must not be so strong as to prevent separation of the collapsed lumen walls under urinary bladder pressure when the patient needs to empty his or her bladder. The selection and optimization of operative materials and coatings is a matter of ordinary skill in the art.

Figure 3:
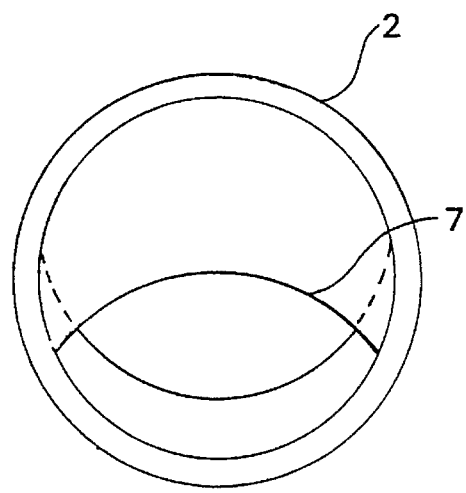
FIG. 3 is an enlarged sectional view taken on line I—I of FIG. 1.

In the preferred embodiment shown in FIGS. 1 and 2, the drainage duct 1 comprises multiple unidirectional valve means 7, including a valve means 7 positioned at the inlet or proximal end 4. The unidirectional valve means 7 prevents urine back flow and bacterial ingress into the bladder, thereby further minimizing the likelihood of urinary tract infection. The unidirectional valve 7 consists of multiple flexible flaps attached to the inner tube 3 of the drainage duct 1 and projecting towards the distal or receptacle end of said duct. The flaps are normally closed to prevent reverse flow into the bladder (FIG. 2) but open to permit the flow of urine into the duct under very slight pressure (FIG. 1). FIG. 3 is an enlarged sectional view of a partially opened valve 7.

Figure 4:
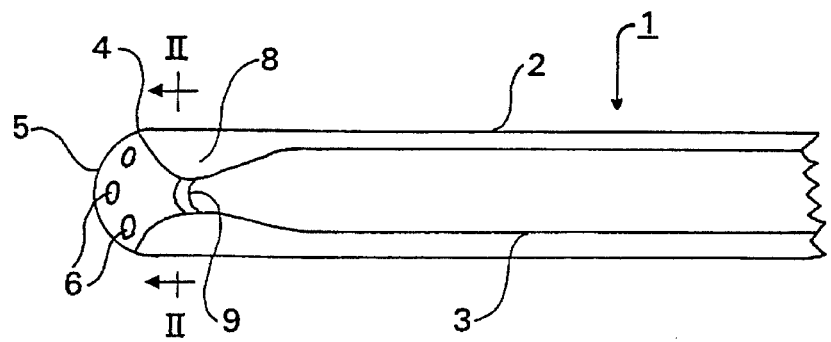
FIG. 4 illustrates an alternative embodiment of the urinary drainage device of the present invention, showing the inner lumen comprising a collapsible neck with an elastic ring.
Figure 5:
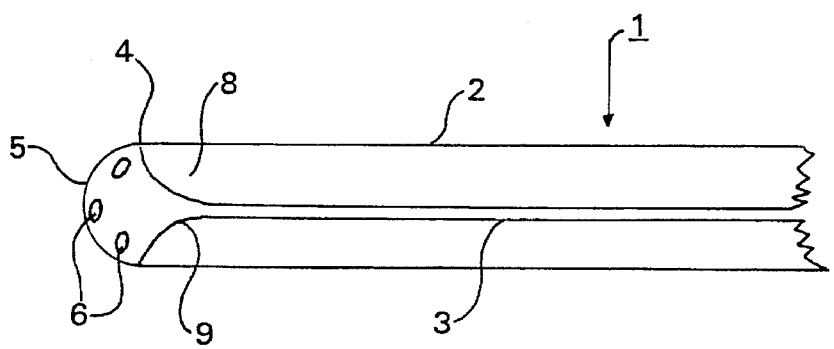
FIG. 5 is a view similar to FIG. 4, but illustrating the collapsible neck in constricted position.
Figure 6:
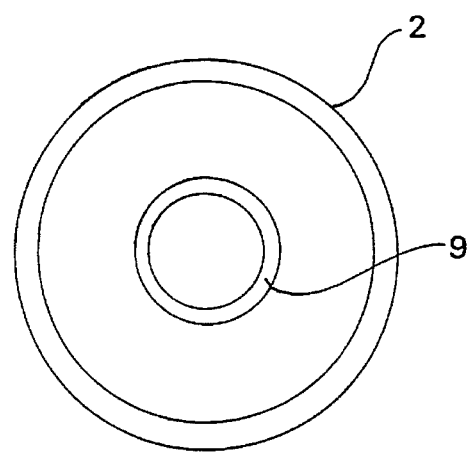
FIG. 6 is an enlarged sectional view taken on Line II—II of FIG. 4.

In the preferred embodiment shown in FIGS. 4 and 5, the inlet or proximal end 4 of the drainage duct 1 has a collapsible neck 8 comprising an elastic ring 9. The elastic ring 9 expands during urination to facilitate urine flow (FIG. 4); it then collapses under normal pressure to prevent urine back flow (FIG. 5). FIG. 6 is an enlarged sectional view of a partially expanded neck. The embodiment shown in FIGS. 4 and 5 further comprises an anchoring means at the proximal end 4 (not shown), such as the expandable elastic collar described above in regard to FIGS. 1 and 2.

Figure 7:
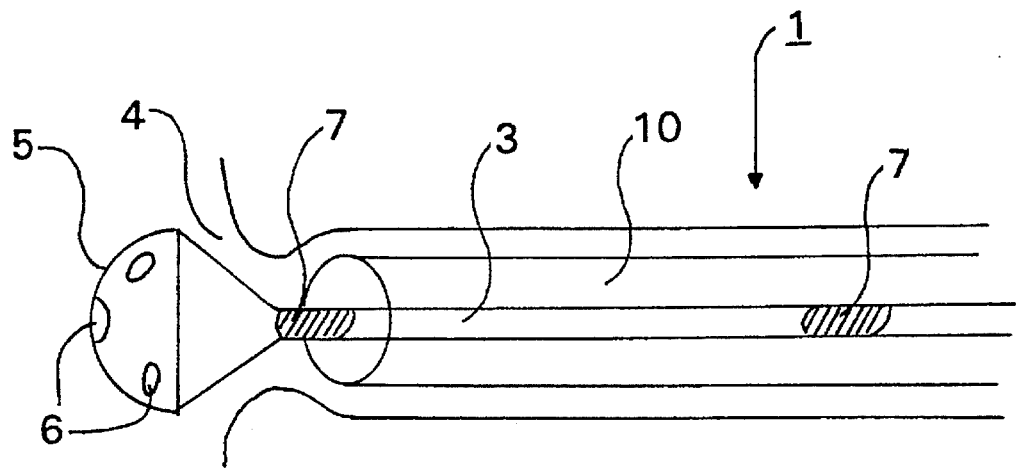
FIG. 7 is a sectional view of an alternative embodiment of the urinary drainage device of the present invention, showing the inner lumen in collapsed position during the removal of the outer catheter tube.
Figure 8:
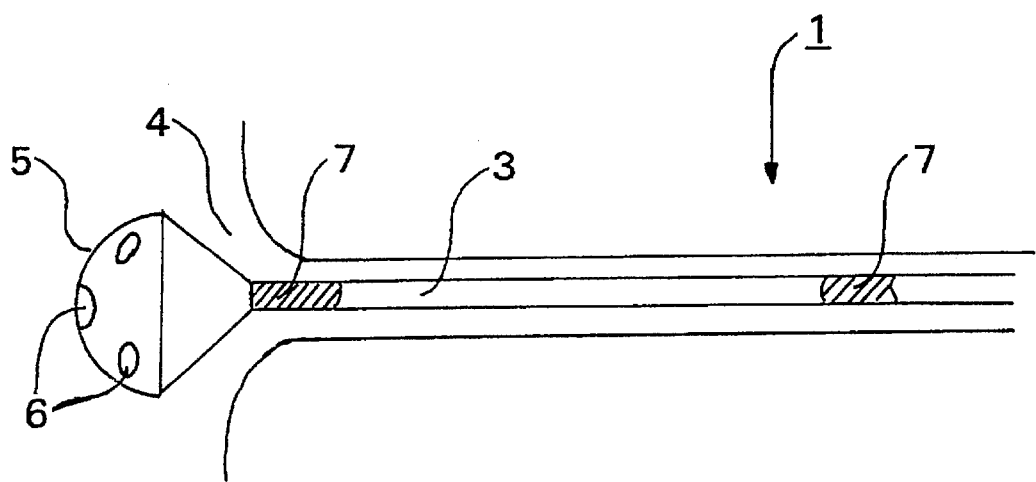
FIG. 8 is a sectional view similar to FIG. 7, following the removal of the outer catheter tube.

FIGS. 7 and 8 illustrate an alternative preferred embodiment of the present invention. In this embodiment, the drainage duct 1 comprises a removable outer tube 10 and a collapsible inner tube 3. The removable outer tube 10 resembles the flexible outer tube 2 of the embodiment illustrated by FIGS. 1 and 2, but can be removed after insertion leaving only the collapsible inner tube 3. The embodiment illustrated in FIGS. 7 and 8 operates under control of the urethral musculature, thus maintaining urinary bladder control during continuous urine collection. The inner tube 3 comfortably conforms to the shape of the urethra, as illustrated by FIG. 8.

Figure 9:
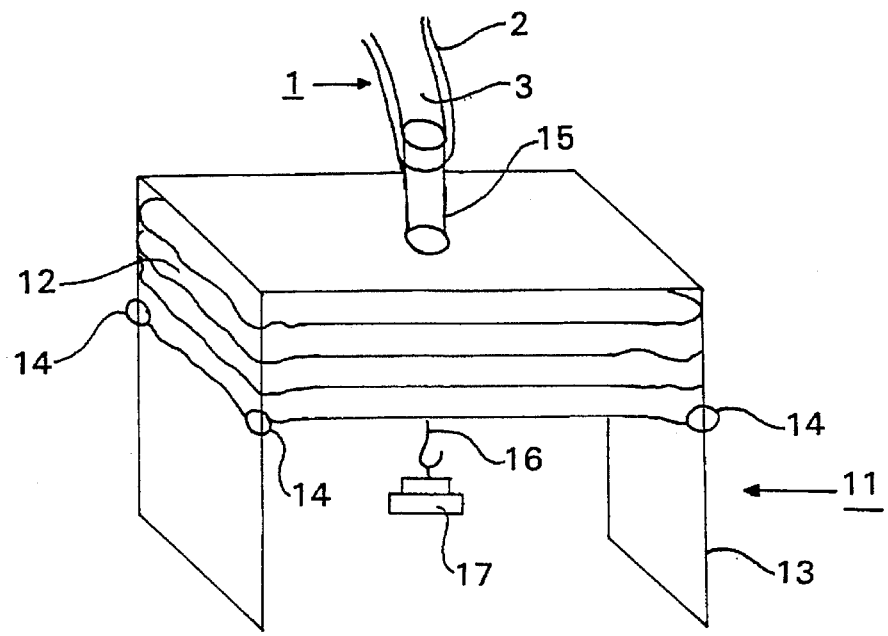
FIG. 9 is a perspective view of the evacuating receptacle of the present invention showing the container in its normal rest position.
Figure 10:
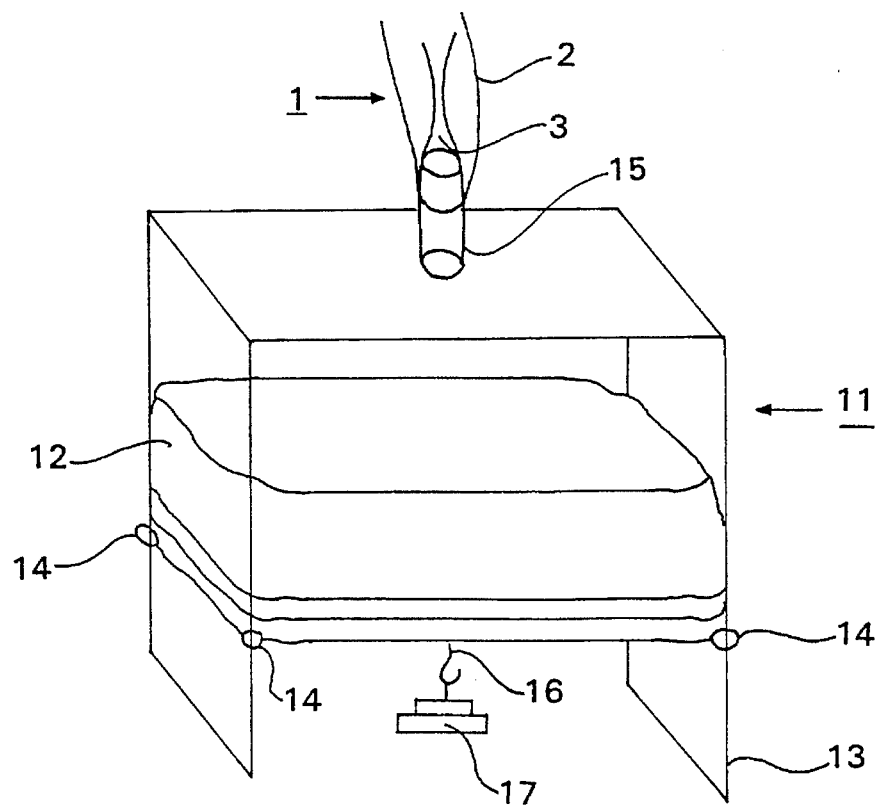
FIG. 10 is a perspective view of the evacuating receptacle of the present invention showing the container in partially expanded position.

FIGS. 9 and 10 illustrate the evacuator-type collection receptacle 11 in the urinary drainage device of the present invention. In the present form of the invention, the evacuator-type collection receptacle 11 comprises a bellows-type collapsible container 12 for receiving and collecting the urine. The bellows-type container 12 is preferably constructed of polyethylene or polypropylene, although it may be made of other impervious resilient materials. In fact, the suctioning may be accomplished using any container capable of producing sufficient negative pressure during evacuation to draw the urine from the drainage duct 1. The bellows container 12 is attached at the top to a rigid support frame 13. The bellows container 12 is further connected to the support frame 13 at its base through suitable sliding means, such as the ring connectors 14 shown in the figures. The collected urine enters the bellows container 12 through a tube connector 15 to which the drainage duct 1 is attached. As the container collects urine, the weight of the additional urine extends the bellows container 12, thereby creating additional partial vacuum to draw additional fluid into the receptacle. If desired, a hook 16 may be incorporated into the base of the collapsible container 12 upon which weights 17 may be hung to increase the suction. When used in combination with the collapsible drainage duct 1 of the present invention, the partial vacuum created during collection facilitates the evacuation and collapse of the inner tube 3.

Obviously, many modifications and variations of the present invention are possible and will be evident to those of ordinary skill in the art. For example, the improved urinary drainage device preferably incorporates the various embodiments described herein, namely a drainage duct comprising a collapsible inner lumen with a collapsible neck or attached unidirectional valves in combination with the evacuator-type collection receptacle. However, each of these embodiments may be used individually or in combination to improve existing drainage devices. It is therefore to be understood that within the scope of the appended claims, the invention may be practiced in ways other than as specifically described herein.

I claim:

1. A urinary drainage device comprising:
   a double-lumen tube for draining urine from a patient, said tube comprising a flexible outer tube and an inner collapsible tube, wherein said inner collapsible tube extends throughout the length of the double-lumen tube, and wherein said flexible outer tube is adapted to be placed within a patient's urethral duct; and
   a collection receptacle connected to said double-lumen tube for receiving urine.

2. The urinary drainage device of claim 1 wherein said double-tube tube further comprises a unidirectional valve means attached to said inner collapsible lumen.

3. The urinary drainage device of claim 2 wherein said unidirectional valve means is positioned near the inlet of said double-lumen tube.

4. The urinary drainage device of claim 2 wherein said unidirectional valve means comprises a plurality of flexible flaps.

5. The urinary drainage device of claim 1 wherein said double-lumen tube further comprises an elastic, collapsible ring positioned at the inlet of said double-lumen tube.

6. The urinary drainage device of claim 1 wherein said inner collapsible tube is formed of a hydrophobic material or has an interior surface coating of a hydrophobic substance.

7. The urinary drainage device of claim 6 wherein said hydrophobic material or hydrophobic substance is a silicone.

8. The urinary drainage device of claim 1 wherein said double-lumen tube has a proximal end and a distal end, wherein said distal end is removably connected to said collection receptacle.

9. The urinary drainage device of claim 8 wherein said proximal end comprises a plurality of apertures.

10. The urinary drainage device of claim 1 wherein said flexible outer tube is removably connected to said inner collapsible tube.

11. A urinary drainage device comprising:
    a double-lumen tube for draining urine from a patient, said tube comprising a flexible outer tube and an inner collapsible tube, wherein said inner collapsible tube extends throughout the length of the double-lumen tube, and wherein said flexible outer tube is adapted to be placed within a patient's urethral duct; and
    a suctioning means connected to said double-lumen tube for suctioning and receiving urine.

12. The urinary drainage device of claim 11 wherein said suctioning means comprises a resilient container which is compressible to create a suctioning force as it returns to its normal expanded condition.

13. The urinary drainage device of claim 12 wherein said resilient container comprises a means to increase the suctioning force created therein.

14. A urinary drainage device comprising:
    a double-lumen tube for draining urine from a patient, said tube comprising a flexible outer tube and an inner collapsible tube, wherein said inner collapsible tube extends throughout the length of the double-lumen tube, and wherein said flexible outer tube is adapted to be placed within a patient's urethral duct; and a suctioning means connected to said double-lumen tube for suctioning and receiving urine, wherein said suctioning means comprises a resilient container which is compressible to create a suctioning force as it returns to its normal expanded condition, and wherein said resilient container has a top portion attached to a rigid support frame and a bottom portion slidably connected to said support frame.

15. The urinary drainage device of claim 14 wherein said bottom portion is slidably connected to said support frame with rings.

* * * * *

UNITED STATES PATENT AND TRADEMARK OFFICE
CERTIFICATE OF CORRECTION

PATENT NO. : 5,505,717

DATED : April 9, 1996

INVENTOR(S) :
Patrick S. Moore

It is certified that error appears in the above-indentified patent and that said Letters Patent is hereby corrected as shown below:

In column 6, line 19, (claim 2) "double-tube tube" should read -- double-lumen tube --.

In column 6, line 20, (claim 2) "lumen" should read --tube--.

Signed and Sealed this

Sixth Day of August, 1996

Attest:

BRUCE LEHMAN

*Attesting Officer*     *Commissioner of Patents and Trademarks*